(12) United States Patent
Carney

(10) Patent No.: US 8,851,082 B2
(45) Date of Patent: Oct. 7, 2014

(54) VAPORIZER FOR WATER PIPE INLET

(71) Applicant: Kevin D. Carney, Los Osos, CA (US)

(72) Inventor: Kevin D. Carney, Los Osos, CA (US)

( * ) Notice: Subject to any disclaimer, the term of this patent is extended or adjusted under 35 U.S.C. 154(b) by 3 days.

(21) Appl. No.: 13/653,651

(22) Filed: Oct. 17, 2012

(65) Prior Publication Data

US 2013/0039639 A1    Feb. 14, 2013

Related U.S. Application Data

(60) Provisional application No. 61/687,916, filed on May 2, 2012.

(51) Int. Cl.
*A24F 5/00* (2006.01)
*A24F 1/30* (2006.01)

(52) U.S. Cl.
USPC .......................................................... 131/226

(58) Field of Classification Search
CPC ..................................... A24F 5/00; A24F 1/30
See application file for complete search history.

(56) References Cited

U.S. PATENT DOCUMENTS

| | | | | |
|---|---|---|---|---|
| 1,734,756 A | * | 11/1929 | Alland | 131/173 |
| 1,761,636 A | * | 6/1930 | Mancusi | 131/197 |
| 1,795,315 A | * | 3/1931 | Quest | 131/210 |
| 1,809,529 A | * | 6/1931 | Pettibone | 131/207 |
| 2,762,375 A | * | 9/1956 | Fessler | 131/194 |
| 4,165,753 A | * | 8/1979 | Stryker | 131/173 |
| 4,303,083 A | | 12/1981 | Burruss, Jr. | |
| 5,778,896 A | * | 7/1998 | Seals et al. | 131/181 |
| 6,095,153 A | | 8/2000 | Kessler | |
| 6,250,301 B1 | | 6/2001 | Pate | |
| 6,295,982 B1 | | 10/2001 | Reed, Jr. | |
| 6,845,771 B1 | | 1/2005 | Love | |

* cited by examiner

*Primary Examiner* — Michael J Felton
(74) *Attorney, Agent, or Firm* — Heisler & Associates

(57) ABSTRACT

The vaporizer assembly includes a nail sub-assembly formed of a high rate of heat transfer material and an adapter assembly formed of a lower rate of heat transfer material. The nail sub-assembly includes a bowl at an upper end and a shaft extending down from the bowl. The shaft has a hollow bore passing therethrough. The nail sub-assembly is preferably formed of a titanium alloy which can be heated to high temperatures without damage thereto. The adapter has a hollow core sized to receive the shaft of the nail therein. The nail is preferably threaded along with portions of the adapter to facilitate height adjustability of the nail relative to the adapter. Lower portions of the adapter are configured to mate with a water pipe inlet tube or other downstream vapor handling device.

7 Claims, 5 Drawing Sheets

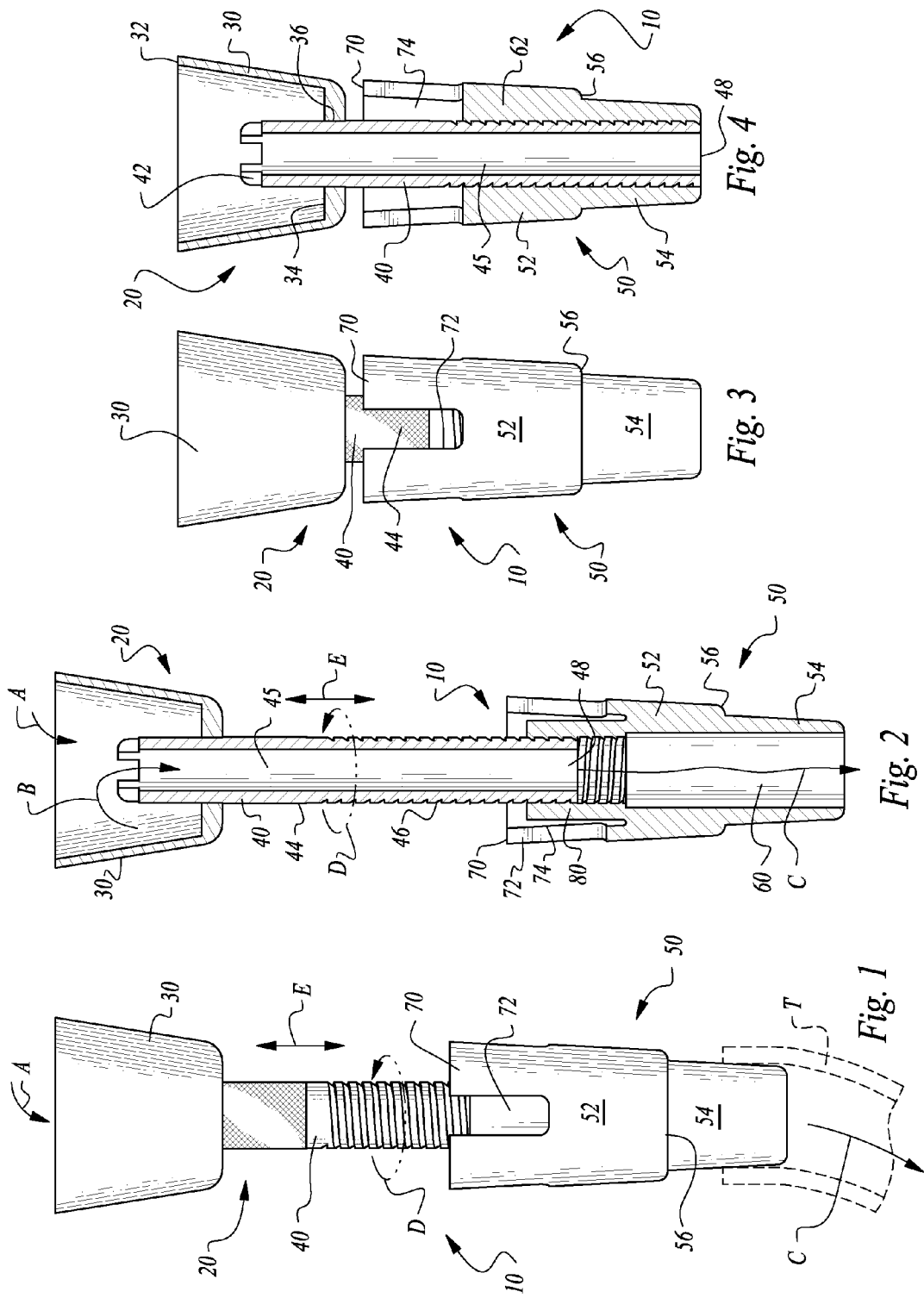

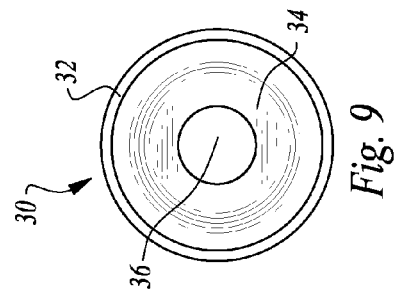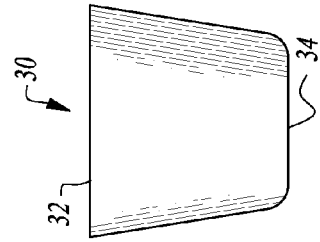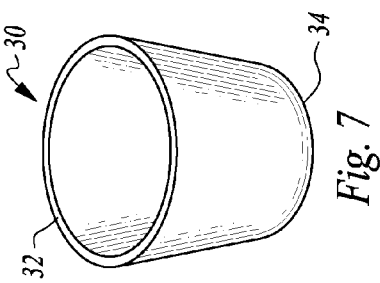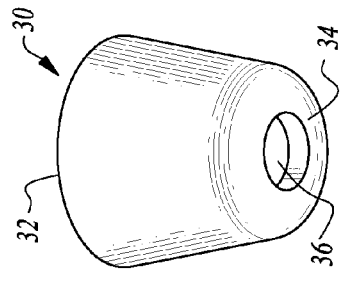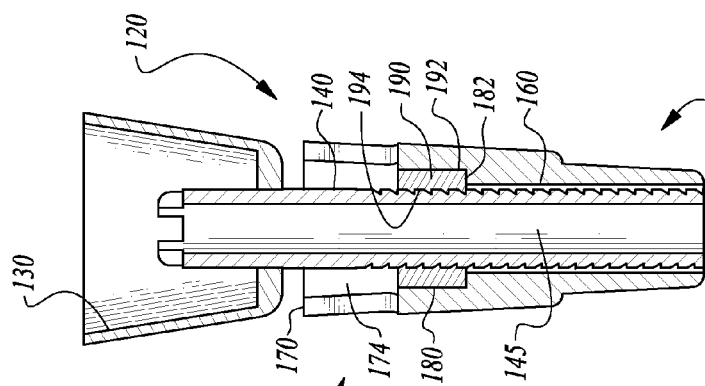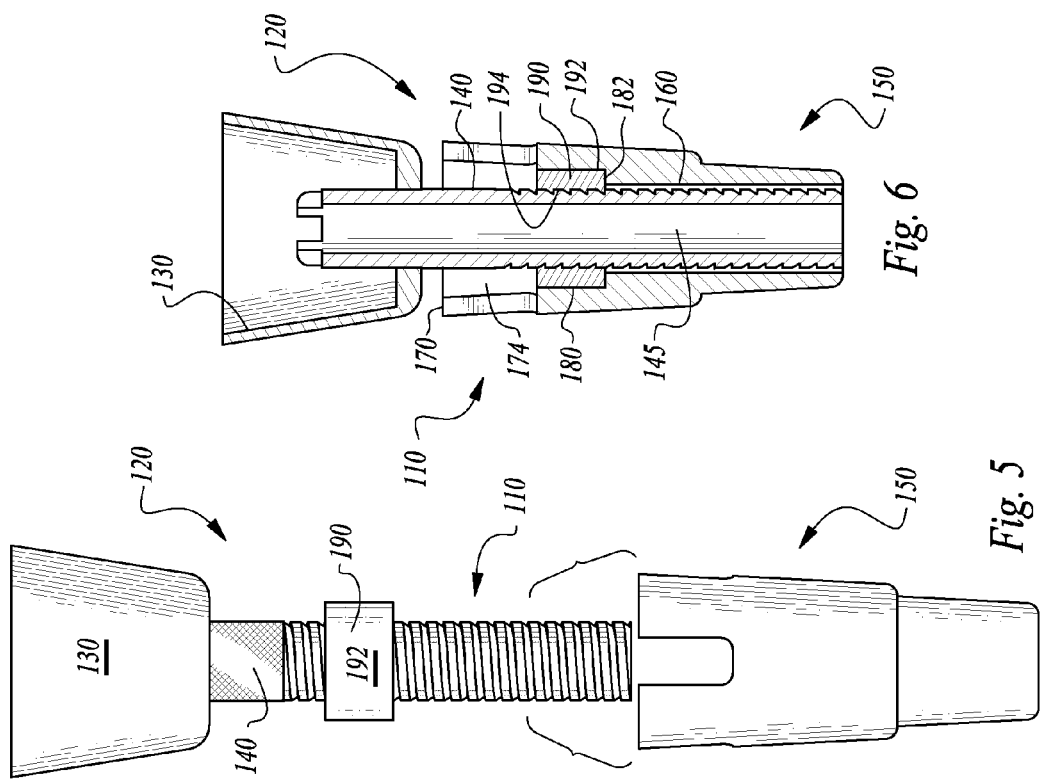

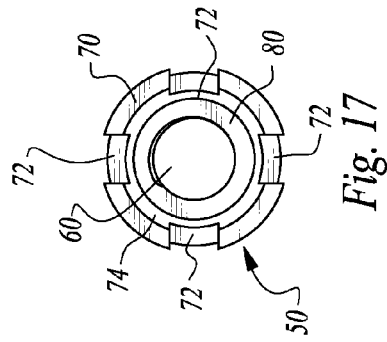
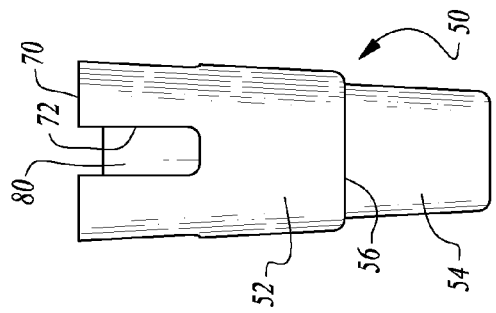
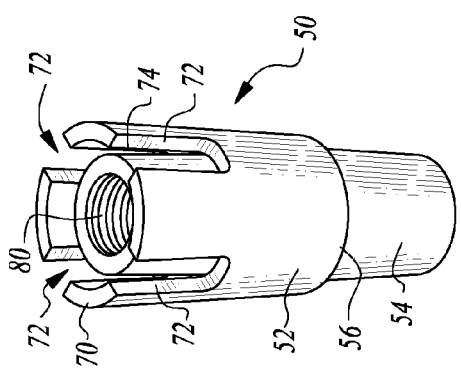
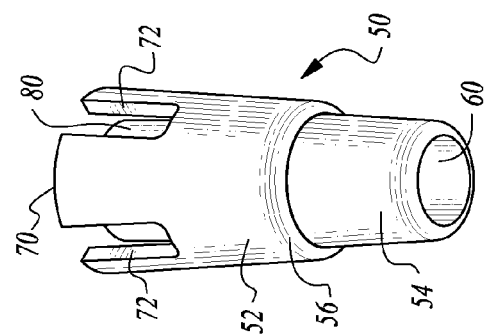
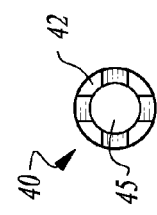
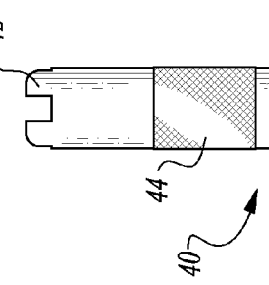
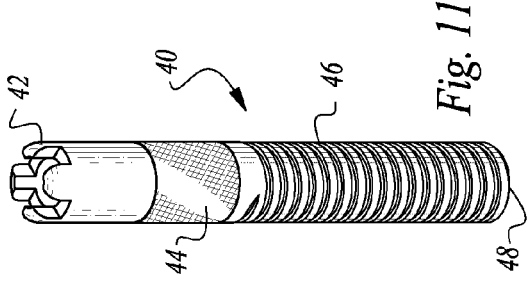
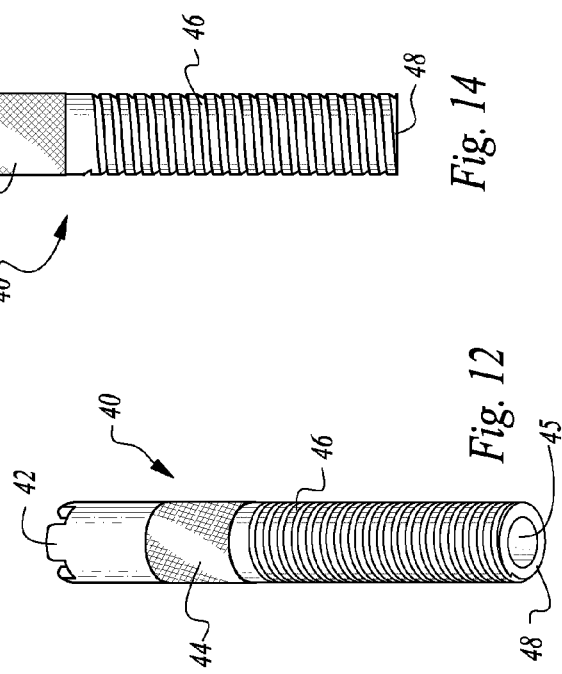

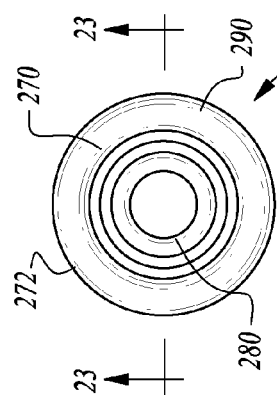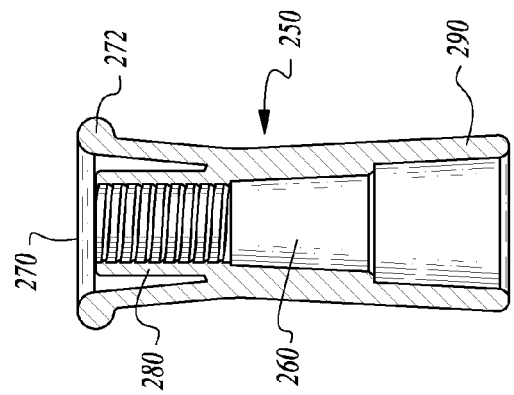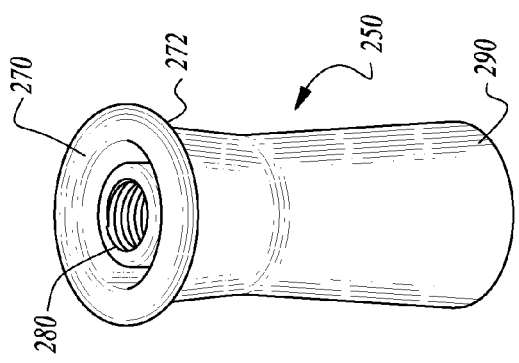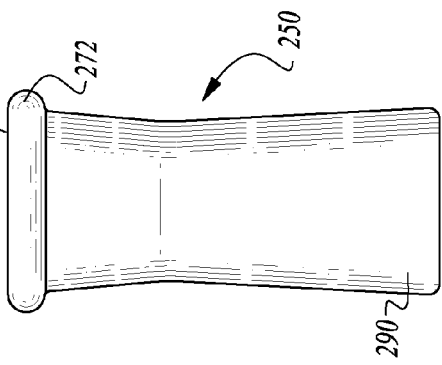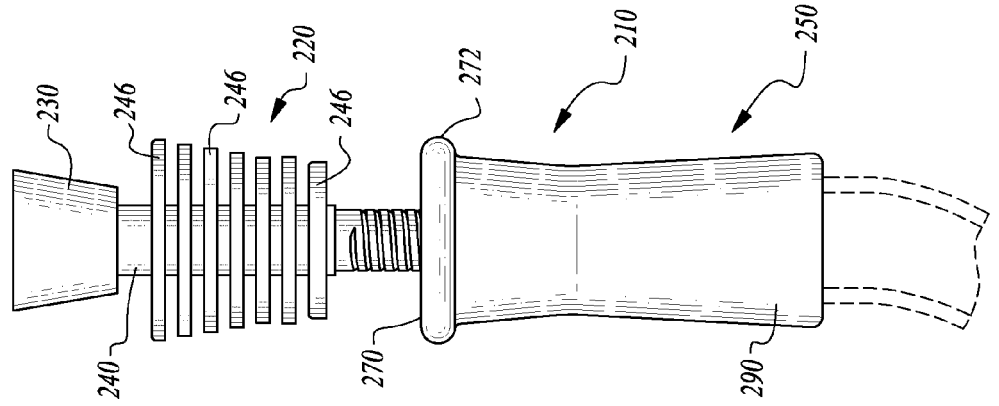

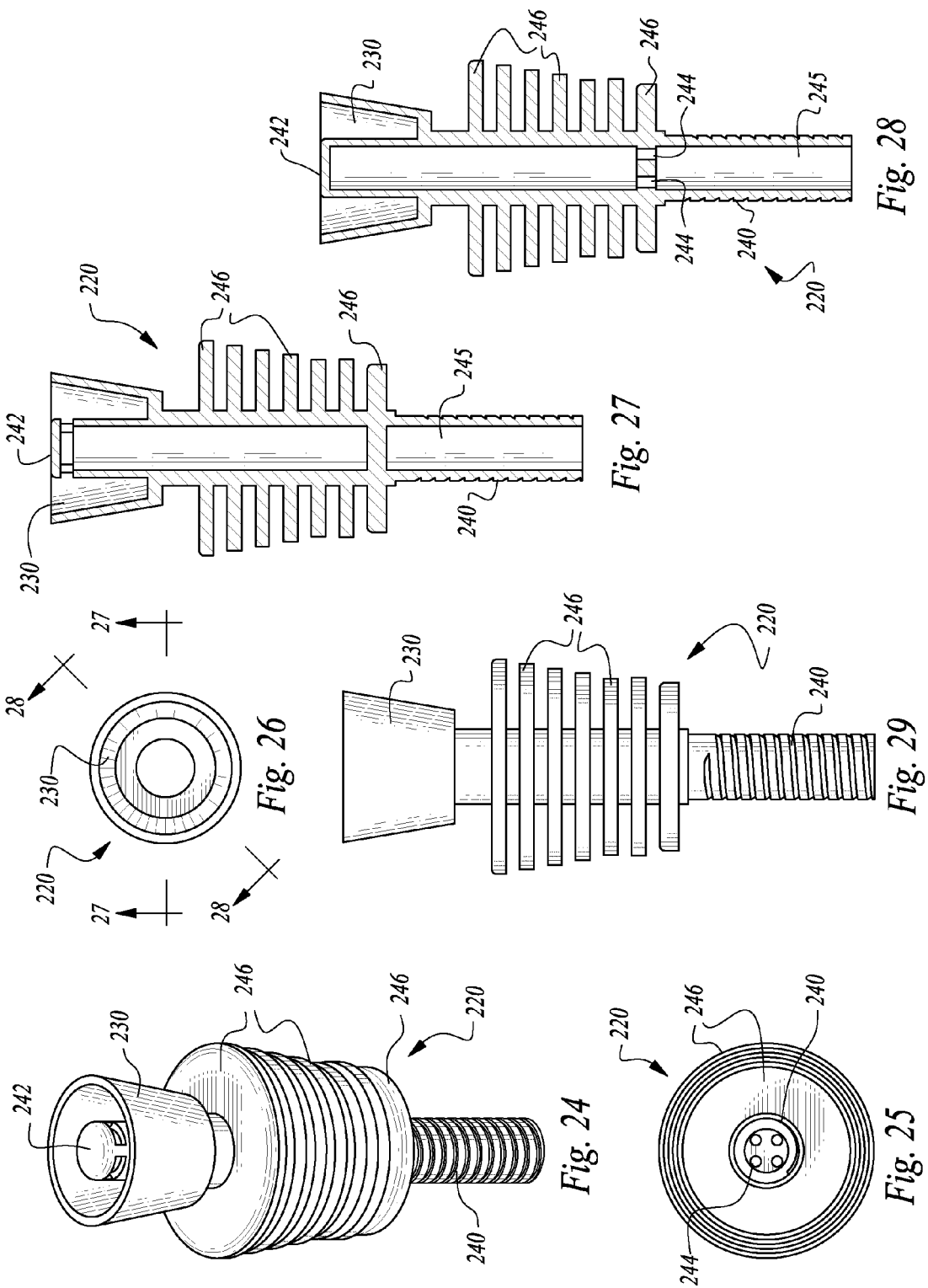

US 8,851,082 B2

VAPORIZER FOR WATER PIPE INLET

CROSS-REFERENCE TO RELATED APPLICATIONS

This application claims benefit under Title 35, United States Code §119(e) of U.S. Provisional Application No. 61/687,916 filed on May 2, 2012.

FIELD OF THE INVENTION

The following invention relates to vaporizers which utilize high heat to take solid or liquid materials and convert them at least partially into a gas, such as for inhalation by a user. More particularly, this invention relates to vaporizers which can be attached to a water pipe inlet or to a nebulizer or other equipment designed for inhalation of vapors produced thereby.

BACKGROUND OF THE INVENTION

Atomization/vaporization of substances is well known for aromatherapy, respiratory therapy, or for smoking activities. While combustion of a solid or liquid substance is one method for production of gas/vapors for inhalation, non-combustion or limited combustion vaporization is also known. This is accomplished though the heating of a selected substance to a temperature at which it undergoes phase change into a gas with no chemical reaction or with different chemical reactions than the basic oxidation/decomposition of hydrocarbon substances into $CO_2$ and water. One known way to so vaporize a substance is to heat a tool until it is of the desired temperature, and then removing it from a heat source before introducing the material which is to be atomized/vaporized. This process allows the material to go though a phase change, called atomization/vaporization instead of being combusted through ignition. Substantial research has established that the atomization/vaporization process is a much healthier, cleaner alternative to combustion.

This invention is intended for any use, limited only by the user's imagination, but its main purpose is for the process of atomization/vaporization of materials. As stated in other patents and shown by the large demand for personal atomizers/vaporizers, there is to date a shortage of well-engineered personal atomizers/vaporizers which are simple to understand and use. Even though there are patents for other devices which accomplish solely vaporization, all of these patents differ in engineering and appearance as well as material and functional properties.

The problem which this invention addresses is the lack of good technology in the industry for simple effective vaporizing/atomizing of essential oils and other solid or liquid substances. All technology to date either employs glass vials which must be screwed into an adaptor and heated up to vaporization temperature, which does not allow continuous use as the users must wait for each to cool down after use before replacing this one used individual glass vial; limiting the efficiency with which the essential oils can be vaporized/atomized.

Another prior art invention relating to this product is a titanium "nail" which is designed to heat up like this product however it requires separate glass adaptors to fit different size water vessels. Such products also require an adaptor, called a "glass dome/oil globe/vapor globe," which must be removed in order to heat the titanium part and again placed on top of another glass adaptor, with the titanium "nail" in-between, in order to use essential oils.

This prior art titanium "nail" has a flat surface on which the essential oils are placed and vaporized. The vapors must then be directed around the outside of the titanium nail by the glass adaptors and funneled down into the correctly sized water vessel.

A need exists for an efficient and revolutionary vaporizer with a self-contained "domeless" function which streamlines and simplifies the process. Users of such a "domeless" device would continue to heat the titanium nail portion and enjoy essential oils without having to remove/replace or unscrew any glass adapters or holders. The user also would enjoy the added ease of not having a "dome" to remove, to heat and then replace.

Other vaporizers use the same type phase change as the atomizer/vaporizer described herein, although other prior art inventions are all limited to vaporizing certain and specific materials. Through exhibiting different processes as well as separate structural engineering, this invention has distinct technology and is able to atomize/vaporize a greater variety of material. Examples of these other devices include:
U.S. Pat. No. 6,295,982 to Reed, Jr., Oct. 2, 2001
U.S. Pat. No. 6,250,301 to Pate, Jun. 26, 2001
U.S. Pat. No. 6,095,153 to Kessler, et al., Aug. 1, 2000
U.S. Pat. No. 4,303,083 to Burruss, Jr., Dec. 1, 1981
U.S. Pat. No. 6,845,771 to Love, Jan. 25, 2005

Though other patents accomplish vaporization, the manufacturing process, designs, as well as functional properties are far from equivalent to this invention.

This invention allows user to enjoy aromatherapy and the vaporization of essential oils without any additional containers, top adaptors or catchments systems which all other systems require, while maintaining a most efficient center column for the vapors to travel through. This product is simply heated and the particulates or essential oils are applied or entered from the top open environment for use. This simplifies the entire process for aromatherapy and the atomization/vaporization of particulates or essential oils.

SUMMARY OF THE INVENTION

This invention uses a funned shape titanium top bowl to increase efficiency, allowing for the quickest vaporization of essential oils though a very high surface area along with a deep catchment basin, allowing it to hold a greater quantity of essential oils at once then any other product. This mechanism catches the vapors from inside the top titanium bowl and pulls them though the center titanium column eliminating the need for outer glass adaptors to trap and direct the vapors into the user's desired glass vessel. Also, the titanium "nail" of this invention has a shaft which is threaded into a ceramic adaptor which serves as a heat sink, allowing the users to continually heat the top of the product without the bottom ceramic adaptor getting too hot to be held in a glass vessel of choice. Due to the recessed angled extrusions on the ceramic adapter, it fits all produced glass vessels at 14/18 mm sizes, such as glass water pipe inlets.

The solid grade 2 titanium construction of the "nail" portion of this invention in its preferred form, allows for even distributed heat which provides faster heating then glass and is more efficient in the vaporization process. The user can change the desired temperature, accommodating a wide rage of possible vaporization needs. With all other products on the market requiring many other adaptors and parts to function, this part can work alone or with a ceramic heat sink to make it adaptable for many more applications.

The invention works by heating up the top material which is preferably made of, but not limited to, grade 2 titanium.

Grade 2 titanium is selected as the main material for use due to its beneficial material properties of high melting point (3*10^3 degrees F.), low thermal expansion (5 microstrain/degrees F.) and low specific heat (0.13 BTU/Lb*F). Titanium has a very low coefficient of thermal expansion and high melting point is extremely beneficial for use because the part can be heated to over 1000 degrees F., and with a low thermal expansion it can be threaded into a ceramic part made of Alumina without over expanding or cracking the ceramic part due to internal stress. This is also due to Alumina's beneficial material properties with a higher melting point then titanium of (3.8*10^3 F.) and a thermal expansion similar to that of titanium at (4.5 microstrain/degrees F.). Grade 2 titanium is also chosen due to its purity and health benefits. Titanium (especially grade 2) does not emit or exhaust any harmful gasses or elements when heated, as do many steels, brasses and coppers, and is considered commercially pure. This makes titanium a good choice for use in vaporization.

The titanium part is preferably made up of two separate machined parts which are joined together into one final part. The top portion of the titanium part is shaped in a bowl shape with thin walls and bottom to allow for quick heating and cooling cycles. Having a thinner thickness of material allows this top part, where the essential oils are applied, to be heated faster and cooled quicker. The bowl shape of this product versus many other designs, which either implement glass tubes or flat surfaces, combines and improves upon preexisting technology. This bowl design allows users the ease of a tube design in allowing this product to be used and implemented at any angle due to the sidewall support which allows use without the essential oils falling out of the unit or off of the hot vaporization surface. Yet also the grade 2 titanium material heats up much faster then any glass would due to its metal characteristics heating much more quickly and efficiently.

The angled top bowl is also more efficient then other designs due to its large surface area created by the catchment basin along with the angled sidewalls. When the top is heated and the essential oils are applied/introduced into the bowl for vaporization, it can run down the entire sidewall vaporizing all the way down as well as in the bottom catchment basin. This is a significant improvement over other titanium nail technology which only implements flat surfaces for the vaporization of essential oils.

The second part of the invention which is fixed to the titanium top bowl is the titanium column/shaft. The titanium shaft is also made of but not limited to grade 2 titanium. This shaft fixtures up into the inside of the top bowl to allow for an interfering of the two parts, creating a "basin" on the bottom of the top bowl. On the bottom of the top bowl is where these two parts are fixed together or laser welded or otherwise bonded or fastened, conjoining them as one part. On the center column, there are a few different designs which have been implemented, the benefits of which will be described below. On the first design a straight column is used with a center hole for the vapors to travel through. This is done so that the center column can remain hot and allow the vapors not to re-condense as they traveled down the center column and out of the part. The bottom of this center column on previous designs has been an angled design to allow it to fit into different water pipes or other vapor handling devices. Other designs have implemented threading down the center column on the outside to both function as heat fins to cool the overall unit and transfer less heat to the bottom of the unit while also allowing users to screw their part into and out of the ceramic adaptor which allows users to use the product at any height while also making it easier to take apart for cleaning or travel. This adjustable height is very important as it allows users to both raise the top titanium bowl when they wish to use the product or thread it down for compact and easy transportation. Also, knurling has been implemented on the top of the center column before the top bowl to allow users easier grip in screwing the titanium part into and out of the ceramic holder/adaptor. The top of the titanium column that fits into the top bowl has slits or angled cuts in the column. These cuts allow for increased airflow and turbulence into the column to improve the overall function of the product.

The ceramic adaptor is currently produced from Alumina but is not limited to this material. This is a beneficial material to use as it acts as a heat sink with the titanium screwed into it, stopping most of the heat which is in the titanium from traveling or shocking the glass of the water pipe inlet or other vapor handling device which this product can sit in. The other purpose of producing these ceramic parts is to allow this titanium vaporizer to fit in a variety of water pipes. Currently there are four different size water pipe adaptors which are commonly produced and sold in the U.S. In having two well designed ceramic adaptors, this one titanium part can fit universally into nearly every water pipe produced. Many other products that are offered only fit one type of water pipe, so an individual must buy at least four separate products to enjoy aromatherapy and vaporization.

OBJECTS OF THE INVENTION

Accordingly, a primary object of the present invention is to provide a device for conveniently vaporizing solid or liquid materials into a vapor for subsequent inhalation.

Another object of the present invention is to provide a vaporizer for an inlet of a water pipe.

Another object of the present invention is to provide a water pipe inlet vaporizer structure which is easy to handle and which effectively contains a material to be vaporized before it is drawn into the water pipe.

Another object of the present invention is to provide a vaporizer for use in generating gases for subsequent inhalation.

Another object of the present invention is to provide a vaporizer assembly for a water pipe inlet which has a high rate of heat transfer vaporizer sub-assembly adjustably attachable to a support adapter, to control an amount of physical contact between the sub-assembly and the adapter.

Another object of the present invention is to provide a method for adjusting a position of a vaporizer element relative to a vaporizer holder, to control a position of the vaporizer element relative to a water pipe inlet or other inlet into an inhalation structure.

Another object of the present invention is to provide a method for vaporization of a substance and optionally induction of the vaporized substance into downstream inhalation equipment.

Another object of the present invention is to provide a cost effective, portable, easy to use material atomizer/vaporizer for the home and personal markets.

Another object of the present invention is to simplify the home and personal atomization/vaporization market while consistently producing long lasting and efficient results.

Another object of the present invention is to provide an extremely simple and easy to use product that would take no more than one use if not just a few minutes to master the home atomization/vaporization process.

Another object of the present invention is to simplify the atomization/vaporization process to reduce the previous risks to users that were an issue with all previous designs of home vaporizers that are complex and difficult to understand.

Another object of the present invention is to provide a product to every individual no matter the individual's level of ability: physical, mental and economic. The goal in this is to bridge the gap between a complex process and ease of use to promote understanding.

Other further objects of the present invention will become apparent from a careful reading of the included drawing figures, the claims and detailed description of the invention.

BRIEF DESCRIPTION OF THE DRAWINGS

FIG. 1 is a front elevation view of a vaporizer assembly including a high rate of heat transfer sub-assembly referred to as a "nail" and a low rate of heat transfer assembly referred to as an "adapter" and with portions of an inlet of a water pipe shown in broken lines to illustrate one use of the vaporizer assembly according to a first embodiment of this invention.

FIG. 2 is a full sectional view of that which is shown in FIG. 1 and with the nail portion adjustably moved relative to the adapter portion of the vaporizer assembly.

FIG. 3 is a front elevation view of a slightly modified embodiment of that which is shown in FIG. 1 and with the nail shown in a collapsed position relative to the adapter.

FIG. 4 is a full sectional view of that which is shown in FIG. 3.

FIG. 5 is a front elevation view of a second embodiment vaporizer assembly according to this invention.

FIG. 6 is a full sectional view of that which is shown in FIG. 5, but with the nail portion shown in a lowered position relative to an adapter portion.

FIG. 7 is a perspective view of a bowl portion of the nail of FIGS. 1-4.

FIG. 8 is a lower perspective view of that which is shown in FIG. 7.

FIG. 9 is a top plan view of that which is shown in FIG. 7.

FIG. 10 is a front elevation view of that which is shown in FIG. 7.

FIG. 11 is a perspective view of a shaft portion of the nail of the vaporizer assembly of FIGS. 1-4.

FIG. 12 is a perspective view from below of that which is shown in FIG. 11.

FIG. 13 is a top plan view of that which is shown in FIG. 11.

FIG. 14 is a front elevation view of that which is shown in FIG. 11.

FIG. 15 is a perspective view of the adapter of the vaporizer assembly of FIGS. 1 and 2.

FIG. 16 is a perspective view from below of that which is shown in FIG. 15.

FIG. 17 is a top plan view of that which is shown in FIG. 15.

FIG. 18 is a front elevation view of that which is showing FIG. 15.

FIG. 19 is a front elevation view of a second alternative vaporizer assembly according to this invention and shown attached to a water pipe inlet tube shown in broken lines.

FIG. 20 is a perspective view of an adapter of the vaporizer assembly of FIG. 19.

FIG. 21 is a front elevation view of that which is shown in FIG. 20.

FIG. 22 is a top plan view of that which is shown in FIG. 20.

FIG. 23 is a full sectional view of that which is shown in FIG. 20.

FIG. 24 is a perspective view of the nail portion of the second alternative vaporizer assembly of FIG. 19.

FIG. 25 is a bottom plan view of that which is shown in FIG. 24.

FIG. 26 is a top plan view of that which is shown in FIG. 24.

FIG. 27 is a full sectional view of that which is shown in FIG. 24, taken along lines 27-27 of FIG. 26.

FIG. 28 is a full sectional view of that which is shown in FIG. 24, taken along lines 28-28 of FIG. 26.

FIG. 29 is a front elevation view of that which is shown in FIG. 24.

DESCRIPTION OF THE PREFERRED EMBODIMENT

Referring to the drawings, wherein like reference numerals represent like parts throughout the various drawing figures, reference numeral 10 is directed to a vaporizer assembly (FIGS. 1-4). The vaporizer assembly 10 can be fitted into a pipe inlet tube T of a water pipe for supply of vapors into a water pipe, or can be otherwise used, such as merely resting upon a horizontal surface, to vaporize a solid or liquid substance into gaseous vapors suitable for inhalation.

Solid or liquid substances to be vaporized are inserted into a highly heated basin portion at an upper end of the vaporizer assembly 10 (along arrow A of FIGS. 1 and 2). An upper portion of the vaporizer assembly is provided by a high rate of heat transfer sub-assembly referred to as a "nail" and which is preferably formed of a titanium alloy. This nail 20 is heated to a sufficiently high temperature that contact with surfaces of the basin will result in vaporization of the material. Vapors are then drawn, along arrow B of FIG. 2, down into a hollow bore 45 of the nail 20. This passage of vapors continues on down through an adapter 50 by way of a hollow core 60 (along arrow C of FIGS. 1 and 2), before optionally passing into the pipe inlet tube T of a water pipe or into some other apparatus which utilizes vapors.

In essence, and with particular reference to FIGS. 1-4, basic details of the vaporizer assembly 10 are described, according to this first exemplary embodiment. The vaporizer assembly 10 generally includes two parts including a high rate of heat transfer sub-assembly and a low rate of heat transfer sub-assembly. The high rate of heat transfer sub-assembly is referred to as a nail 20 in that it is somewhat nail-like in appearance with a bowl 30 defining a head portion and a shaft 40 extending downward from the bowl 30. The shaft 40 includes a bore 45 passing therethrough such that the shaft 40 is hollow.

The adapter 50 includes a hollow core 60 which can receive the shaft 40 therein. Preferably, the shaft 40 is threaded along with the hollow core 60, in a complementary fashion, such that rotation of the nail 20 (along arrow D of FIGS. 1 and 2) causes adjustment of a position of the nail 20 up and down (along arrow E of FIG. 20) relative to the adapter 50. A rim 70 preferably extends up from an upper body of the adapter 50 to provide a portion of the adapter 50 which can be held (at least indirectly) by a user and which can be less hot as it defines a portion of the adapter 50 more distant from areas where the nail 20 comes into contact with the adapter 50. FIG. 2 shows a threaded collar 80 inboard of the rim 70 which is threaded complementally with threads on the shaft 40. As a slight alternative, FIG. 4 depicts a variation where the entire hollow core 60 is threaded with inner threads 62, rather than providing a separate threaded collar 80 (FIG. 2).

More specifically, and with continuing reference to FIGS. 1-4 and 7-18, specific details of the vaporizer assembly 10 are described defining one form of an element for vaporizing a non-gas substance, according to this first exemplary embodiment. The nail 20 sub-assembly is preferably entirely formed of a titanium alloy. Most preferably, the basin portion defined by the bowl 30 is formed separately from the shaft 40 and the two are press fit together. Alternatively, the bowl 30 could thread onto the shaft 40 with complementary threads provided on portions of the bowl 30 and the shaft 40 for this purpose. As another alternative, the bowl 30 and shaft 40 could be formed together as an integral unit. Preferably, contact between the bowl 30 and shaft 40 is sufficient to facilitate conduction heat transfer between the bowl 30 and shaft 40 such that they maintain a similar temperature. By forming the nail 20 of a titanium alloy, the nail 20 can be heated to exceptionally high temperatures, even approaching or exceeding 3,000° F., for effective vaporization of a variety of different substances.

The bowl 30 is preferably an open topped enclosure including a substantially planar floor 34 with side walls extending up to a lip 32. The hole 36 is formed in the floor 34, preferably near a midpoint thereof, and which floor preferably has a circular form. The shaft 40 can thus extend up through this hole 34 and preferably extends up into the bowl 30 somewhat, but below the lip 32 and above the floor 34. The bowl 30 preferably has side walls which taper slightly so that the lip 32 is circular in form and wider than the floor 34. The opening inboard of the lip 32 defines an entrance into the bowl 30 into which substances to be vaporized can be placed (such as along arrow A of FIGS. 1 and 2).

The shaft 40 is an elongate rigid structure extending from an upper tip 42 to a lower tip 48. A bore 45 passes from the upper tip 42 to the lower tip 48 to provide a hollow vapor input path from the bowl 30. Preferably, a knurled band 44 is provided on a portion of the shaft 40 closer to the upper tip 42 than to the lower tip 48, and configured just below where the shaft 40 passes through the hole 36 in the bowl 30. The knurled band 44 defines a portion of the shaft 40 which can be securely gripped by a user, such as to facilitate rotation (about arrow D of FIGS. 1 and 2) to adjust a height of the nail 20 relative to the adapter 50 (along arrow E of FIGS. 1 and 2). Such height adjustment can alter the rate at which the nail 20 portion cools, adjusting vaporizer 10 performance.

The shaft 40 has outer threads 46 provided on portion of the shaft 40 below the knurled band 44. These outer threads 46 are complemental with threads which are either on the adapter 50 itself or fixed relative to the adapter 50, such that rotation of the nail 20 (about arrow D of FIGS. 1 and 2) causes movement toward and away from the adapter 50 (along arrow E of FIGS. 1 and 2). In one embodiment, these outer threads 46 are acme threads. The outer threads 46 can be sized with sufficient clearance so that even when significant temperature changes are being countered by the shaft 40, sufficient tolerance is still provided for ready rotation of the nail 20 and associated shaft 40 relative to the adapter 50.

While the threads 46 provide part of a preferred form of a means to adjust position of the nail 20 relative to the adapter 50, other position adjustment means could alternatively be provided. For instance, a clamp could releasably grasp the shaft 40 at a desired height, inserts could be intermediately placed in various sizes or numbers to space the nail 20 a desired distance from the adapter 50. The adapter could be provided with nail rests which could be adjustably placed where desired to control a position of the nail 20 relative to the adapter 50.

With continuing reference to FIGS. 1-4, details of the adapter 50 are described, providing a holder for the shaft 40 of the nail 20 according to this first exemplary embodiment. The adapter 50 is preferably a rigid monolithic structure formed of a lower rate of heat transfer material than that from which the nail 20 is formed. In a preferred embodiment this material is a ceramic material, such as an aluminum oxide ceramic material. The adapter 50 generally includes an upper body 52 and a lower body 54. A step 56 preferably is provided between the upper body 52 and the lower body 54. The lower body 54 is sized to fit within an end of a pipe inlet tube T (FIG. 1) and the upper body 52 typically is sized larger than a diameter of the pipe inlet tube T, such that the adapter 50 can have the lower body 54 fit into the pipe inlet tube T, but the upper body 52 is sized large enough to keep the adapter 50 from extending too far into the pipe inlet tube T.

A hollow core 60 in the form of a through bore passes vertically through a center of the adapter 50. This hollow core 60 is sized to allow the shaft 40 of the nail 20 to pass therethrough. In one variation (FIGS. 3 and 4) inner threads 62 are provided on this hollow core 60 which are sized to coact with the outer threads 46 on the shaft 40 of the nail 20. As an alternative, a threaded collar 80 can be provided within the upper body 52 which has threads therein to coact with the outer threads 46 in the shaft 40.

With either variation, the upper body 52 preferably features a rim 70 extending upwardly from the upper body 52 and with slits 72 extending vertically through the trim 70. The rim 70 defines a portion of the upper body 52 of the adapter 50 which is a significant distance from locations where the adapter 50 is in contact with the nail 20, for conduction heat transfer. Because the adapter 50 is formed of a material with a relatively low rate of heat transfer, and with slits 72 in the rim 70, upper portions of the rim 70 will tend to be a significantly lower temperature than other portions of the adapter 50 and relative to a temperature of the nail 20. In some instances, a user might be able to directly hold the adapter 50 at this rim 70 portion. In other instances, a user with relatively lightweight gloves or other limited additional thermal insulation can readily handle the adapter 50 through the rim 70, even when the nail 20 is exceptionally hot. A gap 74 inboard of the rim 70 helps to isolate the rim 70 from portions of the adapter 50 which are in direct contact with the nail 20, to thus further insulate the rim 70 from temperatures associated with the nail 20.

With particular reference to FIGS. 5 and 6, details of an alternative vaporizer assembly 110 are described. With this alternative vaporizer assembly 110, the adapter 150 does not include threads directly thereon. Rather, a recess 180 is provided into which a nut 190 can be located. This nut 190 has an outer surface 192 which fits within the recess 180, so that the nut 190 can be wedged (or merely rest) into the recess 180 and resting upon a ledge 182 defining a bottom of the recess 180.

The nut 190 includes an inside threaded hole 194 which is sized to coact with the outer threads of the nail 120. The nail 120 is similar to the nail 20 of the embodiment of FIGS. 1-4, with a bowl 130 at an upper end and a shaft 140 extending down from the bowl 130, and with a bore 145 within the shaft 140. Threads on an outer surface of the shaft 140 coact with the inside threaded hole 194 of the nut 190 which is secured to (or resting within) the adapter 150. The adapter 150 includes a hollow core 160 to accommodate the shaft 140 and with a rim 170 extending upward to define upper portions of the adapter 150, and with a gap 174 inboard of the rim 170.

With the alternative vaporizer assembly 110, it is not required that threads be formed in the material forming the adapter 150. Furthermore, if the nut 19 is formed of a titanium alloy similar to the material forming the nail 120, various differences in materials which might alter performance can be avoided, such as differing rates of thermal expansion, so that a smooth threading interface can be maintained at a variety of different temperatures. The nut 190 would typically have an outer surface 192 which is knurled or otherwise roughened so that it tends to engage the surfaces of the recess 180 within the adapter 150. As an alternative, the recess 180 and outer surface 192 of the nut 190 can be somehow keyed or faceted in a complementary fashion to prevent relative rotation therebetween. As a further alternative, some form of adhesive or other bonding agent could be utilized to secure the nut 190 within the adapter 150.

In one use mode, the nail 120 is height adjusted while in the adapter 150 by rotation. In another use mode, the nail 120 is removed from the adapter 150 and the nut 190 is rotated to a desired position and then the nail 120 and nut 190 are replaced into the adapter 150.

With particular reference to FIGS. 19-29, details of a second alternative vaporizer assembly 210 are described. With this second alternative vaporizer assembly 210, an alternative nail 220 is provided with a bowl 230 at an upper end and a shaft 240 extending down from the bowl 230. An adapter 250 is provided to support the nail 220. This adapter 250 features a hollow core 260 with a rim 270 extending upward to define upper portions of the adapter 250. A threaded collar 280 is provided within the adapter 250 which is threaded to coact with threads on the shaft 240 of the nail 220.

Uniquely with this second alternative vaporizer assembly, the shaft 240 preferably includes a covered upper tip 242. Slots in a side of the shaft 240 just below the upper tip allow for vapors to be drawn into the hollow bore of this shaft 240. Such a covered upper tip 242 can prevent material from falling down into the bore in the shaft 240 potentially without having sufficient time for the material to vaporize. The bore 245 can also include a barrier with port holes 244 therein to further insure that material does not fall through the bore 245 without becoming vaporized. FIGS. 27 and 28 are similar to each other but show the nail 220 portion at different radially opposed orientations to illustrate the various slots and holes which are only visible in certain sectional views in this particular embodiment.

Annular fins 246 are also optionally shown extending radially from the shaft 240 of the nail 220. These annular fins 246 could be provided on any of the nail embodiments such as the nail 20 (FIGS. 1-4) and the nail 120 (FIGS. 5 and 6). These annular fins 246 potentially increase surface area on the nail 220 for more rapid heating and cooling of the nail 220. Also, such annular fins 246 allow the nail 220 to be more readily directly handled with less thermal protection.

The adapter 250 is configured to include an outer skirt 290 which tapers to a wider form at a lower end thereof opposite to a configuration of the adapter 50 (FIGS. 1-4). This outer skirt 290 is sufficiently wide so that it can rest over an outer portion of a pipe inlet tube T (FIG. 19) so that the adapter 250 overlies the pipe inlet tube T, rather than fitting inside the pipe inlet tube T as with the adapter 50 (FIG. 1). The outer skirt 290 could optionally rest upon a horizontal surface if the vaporizer assembly 210 is not coupled to a water pipe or other downstream equipment. Furthermore, the rim 270 features a lobe 272 which can facilitate the adapter 250 being more readily held by a user's hand, or by some other holding mechanism upon which this lobe 272 can rest.

The various different unique features of the alternative embodiments for the vaporizer assembly 10, 110, 210 can be individually included in the various other alternative embodiments of this invention disclosed herein.

In use and operation, a user will initially remove the nail 20 from the adapter 50 and place the nail 20 adjacent to a heat source. The nail 20 is heated, typically until the material from which the nail 20 is formed is glowing red (or other colors generally indicative of the degree of heating of the nail 20). If desired, the nail 20 can remain within the adapter 50 during this heating process with heat directed to the bowl 30 portion of the nail 20 and allowed to transfer through conduction heat transfer to other portions of the nail 20.

A material to be vaporized is then placed within the bowl 30. This material can be solid or liquid. When the material to be vaporized comes into contact with surfaces of the nail 20, the extreme temperature differential causes rapid phase change of the material into a gaseous vapor. In some instances the material undergoes some degree of chemical reaction, such as an oxidation reaction or other reaction which is driven by the high temperature which the material attains, as well as the material's contact with oxygen or other elements in the air, or other substances which might be present (e.g. water). In other instances, the material is merely heated so that it undergoes a phase change from solid or liquid into gaseous. The resultant vapor is in the generally proximity of the bowl 30. Through suction forces down through the pipe inlet tube T, these vapors are drawn through the bore 45 and the shaft 40 of the nail 20 and down into the pipe inlet tube T (arrows B and C). If the vaporizer assembly 10 is utilized merely resting upon a horizontal surface, the vapors merely emanate out of the bowl 30 into a surrounding environment.

While a pipe inlet tube T is shown such as might be provided on a water pipe, a respirator, nebulizer, or other device for supporting the delivery of vapors to a user for inhalation, might be utilized along with the vaporizer assembly 10 of this invention, as well as the vaporizer assemblies 110, 210 of alternative embodiments. The nail 20 can be rotated relative to the adapter 50 to provide a desired degree of nesting between the nail 20 and adapter 50. Such adjustment might be provided to alter a rate at which the nail 20 cools, or to change the distance through the overall assembly 10. In one embodiment with the alternate vaporizer assembly 110, the nut 190 is first adjusted into a desired position on the shaft 140 in advance of heating. When the nail 120 has been heated the nail 120 can be dropped into the adapter 140 and will drop into a desired distance when the nut 190 drops into the recess 180. In such an embodiment position adjustment occurs by rotating of the nut 190 upon the shaft 140 until it is at a desired position, rather than rotating the nail 120 after it has been nested into the adapter 150.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A vaporizer, comprising in combination:
a titanium alloy structure having an elongate shaft portion and a basin portion; said shaft portion having an upper tip opposite a lower tip; said shaft portion having a hollow bore extending from said upper tip to said lower tip;
said basin portion adjacent said upper tip of said shaft;
said basin portion having a side wall extending up from a floor to a lip, with said shaft passing through said floor;
wherein an adapter is provided formed of a material having a lower rate of heat transfer than said titanium alloy structure, said adapter having a hollow core sized to receive said shaft portion of said titanium alloy structure therein; and wherein said shaft has threads on an outer surface thereof, wherein a nut is provided and formed with an inside threaded hole sized to coact with the threads of the shaft, and wherein the adapter has a recess into which the nut can be received, and wherein said nut can be rotated to a desired position and the nut be replaced into the recess such that the distance between the basin and the adapter can be adjusted.

2. A vaporizer, comprising in combination:

a basin having walls extending up from a floor to a lip;

an elongate shaft having an upper tip extending through said floor into said basin;

said shaft having a hollow bore from said upper tip to a lower tip;

wherein said floor is substantially planar with a circular perimeter;

wherein said upper tip extends through a center of said floor spaced from said perimeter;

wherein said walls taper at a substantially constant angle as they extend up from said lower end to said lip;

wherein said upper tip of said shaft extends at least about halfway up from said floor to a height of said lip;

wherein said hollow bore has a substantially constant cross-sectional diameter along its entire length, wherein said shaft has an outer surface with threads thereon;

a nut with an inside threaded hole sized to coact with the threads of the shaft, an adapter having a hollow core sized to receive said shaft, wherein the adapter having a recess into which the nut can be received, and wherein said nut can be rotated to a desired position and the nut be replaced into the recess such that the distance between the basin and the adapter can be adjusted.

3. The vaporizer of claim 2 wherein said basin and said shaft are formed of a common material having a higher rate of heat transfer than a material forming said holder.

4. The vaporizer assembly of claim 2 wherein said basin and said shaft are formed of a titanium alloy.

5. The vaporizer of claim 3 wherein said basin and said shaft are formed of a titanium alloy and said holder is formed of a ceramic material.

6. The vaporizer of claim 2 wherein a portion of said shaft below said basin is unthreaded and includes knurling thereon.

7. The vaporizer of claim 6 wherein said shaft is longer than a height of said basin.

* * * * *